United States Patent
Tanaka

(10) Patent No.: US 8,961,400 B2
(45) Date of Patent: Feb. 24, 2015

(54) CAPSULE-MEDICAL-DEVICE DEDICATED POWER SOURCE STARTER

(75) Inventor: Shinsuke Tanaka, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 366 days.

(21) Appl. No.: 13/473,000

(22) Filed: May 16, 2012

(65) Prior Publication Data

US 2012/0238811 A1    Sep. 20, 2012

Related U.S. Application Data

(63) Continuation of application No. PCT/JP2010/064777, filed on Aug. 31, 2010.

(30) Foreign Application Priority Data

Nov. 19, 2009  (JP) .................................. 2009-264301

(51) Int. Cl.
*A61B 1/00* (2006.01)
*A61B 1/04* (2006.01)
*A61B 1/06* (2006.01)

(52) U.S. Cl.
CPC ............. *A61B 1/041* (2013.01); *A61B 1/00036* (2013.01); *A61B 1/00144* (2013.01); *A61B 2560/0209* (2013.01)
USPC ............................ 600/118; 600/109; 600/160

(58) Field of Classification Search
CPC .... A61B 1/041; A61B 1/045; A61B 1/00025; A61B 1/00027; A61B 1/00029; A61B 1/00032; A61B 1/00036; A61B 1/05; A61B 1/00158; A61B 2560/0204; A61B 2560/0214
USPC ................................... 600/109, 117, 118, 160
See application file for complete search history.

(56) References Cited

U.S. PATENT DOCUMENTS 7,770,725 B2 *  8/2010  Segawa .......................... 206/363
8,343,038 B2 *  1/2013  Segawa .......................... 600/118
(Continued)

FOREIGN PATENT DOCUMENTS

CN    101119676 A    2/2008
CN    101203169 A    6/2008
(Continued)

OTHER PUBLICATIONS

European Search Report dated Mar. 14, 2013 from corresponding European Application No. 10 83 1384.2.
(Continued)

*Primary Examiner* — Anhtuan T Nguyen
*Assistant Examiner* — William Chou
(74) *Attorney, Agent, or Firm* — Scully, Scott, Murphy & Presser, PC

(57) ABSTRACT

A capsule-medical-device dedicated power source starter that allows switching, by an application of a magnetic field to a magnetic switch that is provided in an inside of a capsule medical device and has a particular sensitivity direction in the magnetic field, a driving of the capsule medical device from an OFF state to an ON state, includes: an insertion part that is formed in a central axis direction and to which the capsule medical device is inserted so that a longitudinal axis direction of the capsule medical device is along the central axis direction; and a magnetic circuit that generates magnetic force lines which are substantially symmetric about the central axis as an axis of symmetry in any planar surfaces including the central axis of the insertion part.

5 Claims, 15 Drawing Sheets

(56) References Cited

U.S. PATENT DOCUMENTS

| | | |
|---|---|---|
| 2004/0254455 A1 | 12/2004 | Iddan |
| 2008/0027267 A1 | 1/2008 | Segawa |
| 2008/0060952 A1 | 3/2008 | Negron |
| 2008/0167523 A1 | 7/2008 | Uchiyama et al. |
| 2009/0192353 A1 | 7/2009 | Segawa |

FOREIGN PATENT DOCUMENTS

| | | |
|---|---|---|
| EP | 1 867 269 A1 | 12/2007 |
| JP | 2002-156247 A | 5/2002 |
| JP | 2003-210395 A | 7/2003 |
| JP | 2004-219191 A | 8/2004 |
| JP | 2004-226345 A | 8/2004 |
| JP | 2004-261240 A | 9/2004 |
| JP | 2005-095433 A | 4/2005 |
| JP | 2006-187424 A | 7/2006 |
| JP | 2006-223473 A | 8/2006 |
| JP | 2007-021039 A | 2/2007 |
| JP | 2007-089893 A | 4/2007 |

OTHER PUBLICATIONS

International Search Report dated Sep. 28, 2010 issued in PCT/JP2010/064777.

* cited by examiner

CAPSULE-MEDICAL-DEVICE DEDICATED POWER SOURCE STARTER

CROSS-REFERENCE TO RELATED APPLICATION

This application is a continuation of International Application No. PCT/JP2010/064777, designating the United States and filed on Aug. 31, 2010 which claims the benefit of priority of the prior Japanese Patent Application No. 2009-264301, filed on Nov. 19, 2009, and the entire contents of the International application and the Japanese Application are incorporated herein by reference.

BACKGROUND OF THE INVENTION

1. Field of the Invention

The present invention relates to a capsule-medical-device dedicated power source starter that allows switching, by an application of a magnetic field to a magnetic switch that is provided in an inside of a capsule medical device and has a particular sensitivity direction in the magnetic field, a driving of the capsule medical device from OFF state to ON state.

2. Description of the Related Art

In recent years, capsule endoscopes having an imaging function and a wireless communication function have appeared in the field of an endoscope. After inserted to an inside of a subject, the capsule endoscopes sequentially capture intra-subject images until excreted from the subject. The capsule endoscopes then wirelessly transmit data of the captured intra-subject images sequentially to an external device provided at an outside of the subject. According to the capsule endoscopes, a doctor, by making a display device display the data of the intra-subject images stored in the external device, is able to make a diagnosis on the inside of the subject based on the intra-subject images.

Some capsule endoscopes include therein a reed switch among the capsule endoscopes, as disclosed in Japanese Patent Application Laid-Open No. 2006-223473, for example. In the capsule endoscope of this type, a magnetic field is applied to a reed switch by putting a power source starter that generates a magnetic field close to a package accommodating the capsule endoscope, so that a driving of the capsule endoscope is switched from OFF state to ON state. In the capsule endoscope provided with the reed switch, it is possible to switch the driving of the capsule endoscope from OFF state to ON state at an arbitrary time and to control an amount of an electrical power consumption of the capsule endoscope.

SUMMARY OF THE INVENTION

According to an aspect of the present invention, a capsule-medical-device dedicated power source starter that allows switching, by an application of a magnetic field to a magnetic switch that is provided in an inside of a capsule medical device and has a particular sensitivity direction in the magnetic field, a driving of the capsule medical device from an OFF state to an ON state, includes: an insertion part that is formed in a central axis direction and to which the capsule medical device is inserted so that a longitudinal axis direction of the capsule medical device is along the central axis direction; and a magnetic circuit that generates magnetic force lines which are substantially symmetric about the central axis as an axis of symmetry in any planar surfaces including the central axis of the insertion part.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

A capsule endoscope system according to an embodiment of the present invention will be explained below with reference to the accompanying drawings.

Entire Configuration of Capsule Endoscope System

Figure 1:
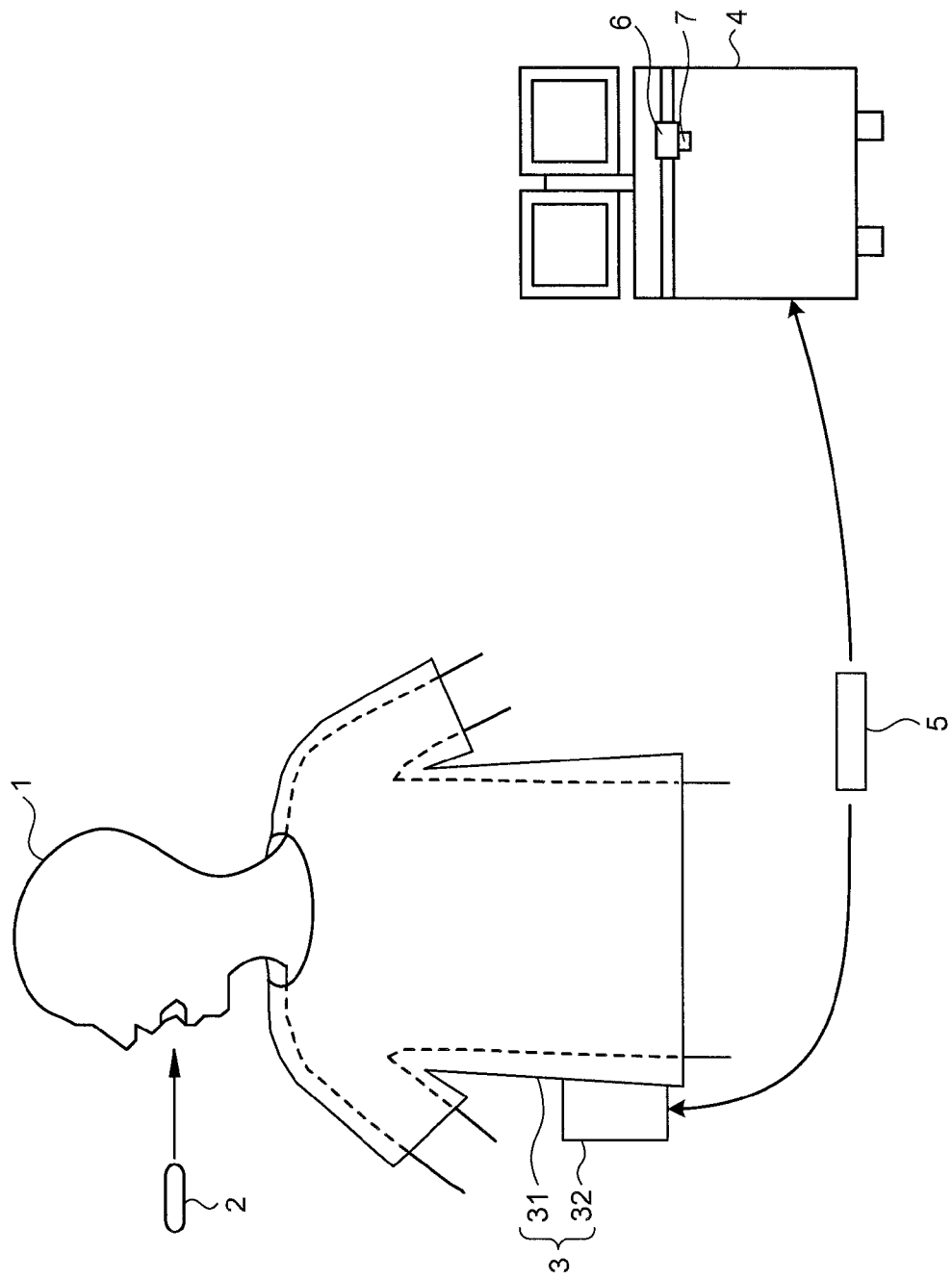
FIG. 1 is a pattern diagram of an entire configuration of a capsule endoscope system according to an embodiment of the present invention.
Figure 2:
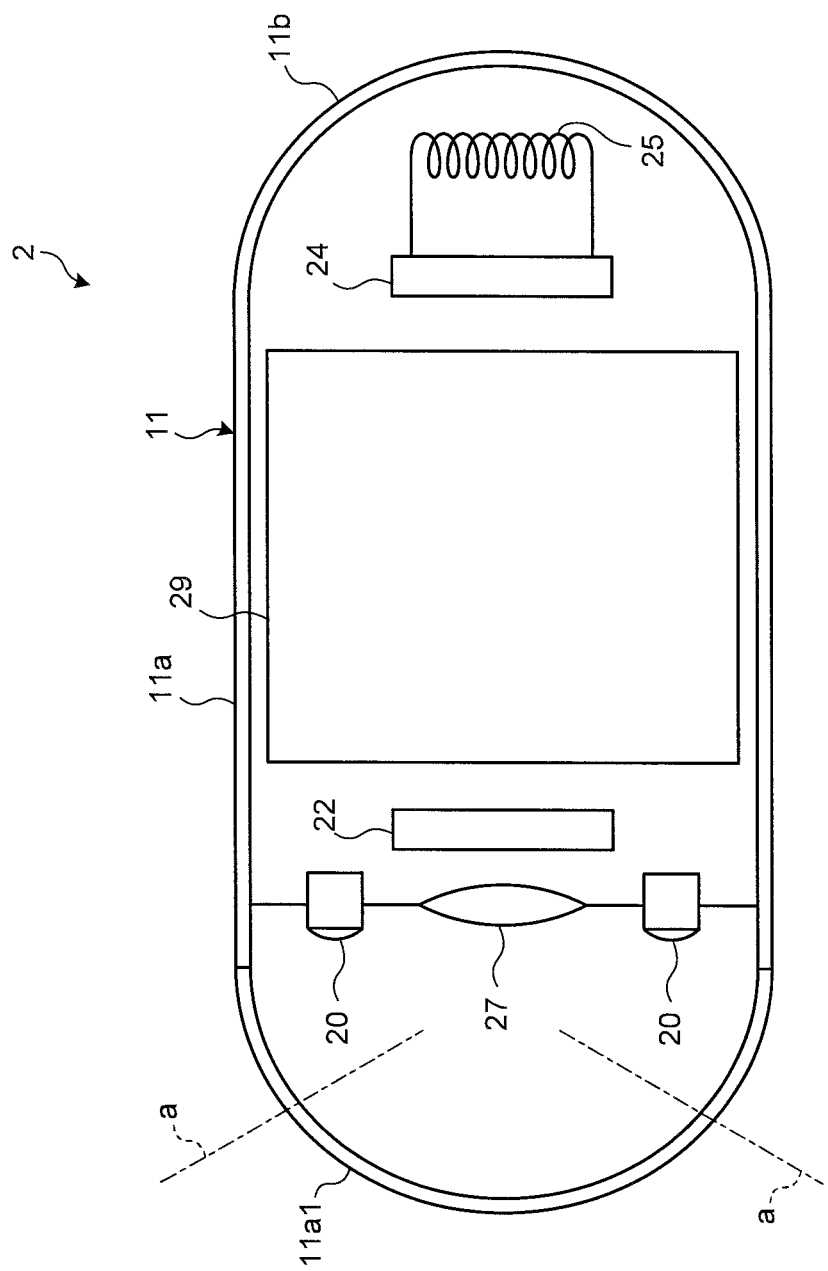
FIG. 2 is a cross-sectional view of a schematic configuration of the capsule endoscope shown in FIG. 1.
Figure 3:
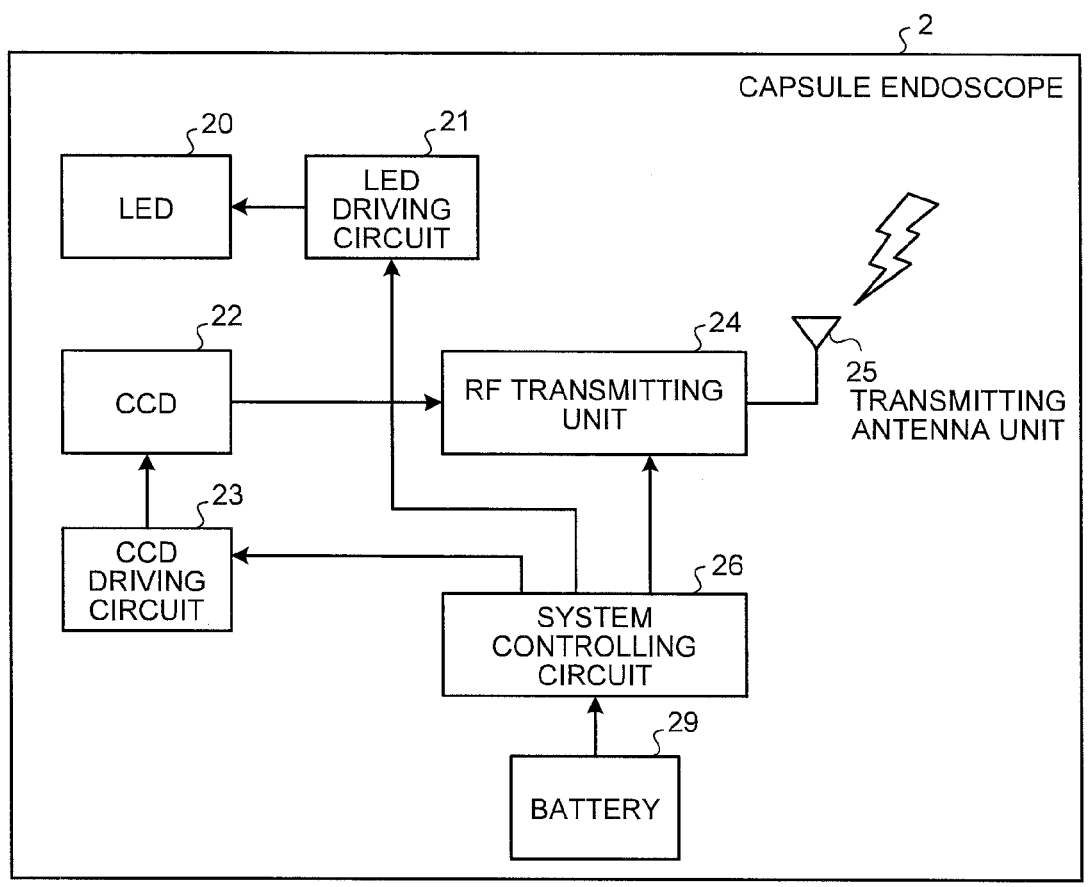
FIG. 3 is a block diagram of an inner configuration of the capsule endoscope shown in FIG. 2.

An entire configuration of a capsule endoscope system according to an embodiment of the present invention will be explained first with reference to FIGS. 1 to 3. FIG. 1 is a pattern diagram of an entire configuration of a capsule endoscope system according to an embodiment of the present invention. FIG. 2 is a cross-sectional view of a schematic configuration of the capsule endoscope shown in FIG. 1. FIG. 3 is a block diagram of an inner configuration of the capsule endoscope shown in FIG. 2.

As shown in FIG. 1, the capsule endoscope system according to the embodiment of the present invention is provided with a capsule endoscope 2 as a capsule medical device inserted to an inside of a subject 1 and a receiver 3 that is arranged in an outside of the subject 1 and performs a wireless communication of various information with the capsule endoscope 2. The capsule endoscope system is also provided with a display device 4 that displays images based on data received by the receiver 3 and a portable recording medium 5 that allows inputting and outputting data between the receiver 3 and the display device 4.

As shown in FIG. 2, the capsule endoscope 2 is provided with an airtight container 11 as an outer case, a plurality of light emitting elements 20 that are provided in the airtight container 11 and emit an illumination light for illuminating an observation site, a solid-state imaging element 22 that receives a reflection light of the illumination light and captures images of the observation site, an imaging lens 27 that forms an image of an object on the solid-state imaging element 22, an RF transmitting unit 24 that modulates image information acquired by the solid-state imaging element 22 into RF signals and transmits the RF signals, a transmitting antenna unit 25 that sends radio waves of the RF signals, and a battery 29.

The airtight container 11 has a size which can be swallowed by a person and forms the outer case sealing the inside thereof in a liquid tight manner by elastically fitting a semi-spherical front head cover 11a and a cylindrical body cover 11b to each other. The front head cover 11a has a semi-spherical dome shape and a rear side of the dome is opened in a circular shape. The front head cover 11a is formed of a transparent member having a transparency or a light permeability and includes a mirror-finished part 11a1 the surface of which is subjected to a mirror finish process, thereby transmitting the illumination light from the light emitting elements 20 to the outside of the airtight container 11 and transmitting the reflection light from the subject by the illumination light to the inside. The mirror-finished part 11a1 is formed in a predetermined mirror finish range (a range indicated by a dashed line indicated by a and a in FIG. 2) determined depending on an imaging range of the solid-state imaging element 22.

The body cover 11b is a member provided at a rear end of the front head cover 11a to cover the components explained above. In the body cover 11b, a cylindrical body part and a rear end part of a semi-spherical dome shape are integrally formed and a front side of the body part is opened in a circular shape. The body cover 11b is made of polysulfon suitable for securing strength and accommodates an illumination unit, an imaging unit, and the battery 29 in the body part and a wireless transmitting unit in the rear end part, the illumination unit, the imaging unit, the battery 29, and the wireless transmitting unit being explained later.

As shown in FIG. 3, the capsule endoscope 2 is provided with an LED 20 as the illumination unit, an LED driving circuit 21 that controls a driving state of the LED 20, a CCD 22 as the imaging unit that captures images of the inside of the subject, the images being the reflection light from an area illuminated by the LED 20 via the imaging lens 27, a CCD driving circuit 23 that controls a driving state of the CCD 22, the RF transmitting unit 24 as the wireless transmitting unit, and the transmitting antenna unit 25.

The capsule endoscope 2 is provided with a system controlling circuit 26 that controls operations of the LED driving circuit 21, the CCD driving circuit 23, and the RF transmitting unit 24, thereby operating so that image data of the observation site illuminated by the LED 20 is acquired by the CCD 22 while the capsule endoscope 2 is inserted to the inside of the subject 1. The acquired image data is converted into RF signals by the RF transmitting unit 24 and transmitted to the outside of the subject 1 via the transmitting antenna unit 25. The capsule endoscope 2 is provided with the battery 29 that supplies an electric power to the system controlling circuit 26 and the system controlling circuit 26 has a function of distributing the driving power supplied from the battery 29 to other components.

The system controlling circuit 26 is provided with a switch element and a latch circuit which have a switching function and are connected between the components and the battery 29. When a magnetic field is applied from the outside, the latch circuit turns on the switch element and holds the ON state thereafter, thereby supplying the driving power from the battery 29 to the components of the capsule endoscope 2. In this embodiment, the imaging unit having an imaging function, the illumination unit having an illuminating function, and the wireless transmitting unit having a wireless function provided in the capsule endoscope 2 are collectively called a function executing unit that executes predetermined functions. Specifically, the components other than the system controlling circuit 26 are the function executing unit that executes given functions set in advance.

As shown in FIG. 1, the receiver 3 serves as a wireless receiving unit that receives image data of the inside of the subject wirelessly transmitted from the capsule endoscope 2. The receiver 3 is provided with a receiving jacket 31 which is worn by the subject 1 and includes a plurality of receiving antennas not shown, and an external device 32 that performs a signal process on the received wireless signals.

The display device 4 serves to display the intra-subject images captured by the capsule endoscope 2 and has a configuration such as a workstation that displays images based on the data acquired by the portable recording medium 5. Specifically, the display device 4 may display images directly by a CRT display device, a liquid crystal display device, and the like or may output the images to another medium like a printer.

In this embodiment, a power source starter 7 having a cylindrical shape is fixed by a fixation tool 6 in an inside of a frame body constituting the display device 4. In turning on the power source of the capsule endoscope 2, a medical staff turns on the power source of the capsule endoscope 2 by inserting the power source starter 7 to a storage case that accommodates the capsule endoscope 2. A configuration of the power source starter 7 and the storage case will be explained later.

The portable recording medium 5 can be connected to the external device 32 and the display device 4 and has a structure capable of outputting or recording information when attached and connected to both. In this embodiment, the portable recording medium 5 is inserted into the external device 32 and records the data transmitted from the capsule endoscope 2 while the capsule endoscope 2 travels in the inside of the subject 1. Next, after the capsule endoscope 2 is excreted from the subject 1, that is, after the imaging of the inside of the subject 1 is finished, the portable recording medium 5 is taken out from the external device 32 and inserted into the display device 4 and the data recorded in the portable recording medium 5 is read out by the display device 4. For example, the portable recording medium 5 is configured by Compact Flash (registered trademark) memory and the like, and inputting and outputting data can be indirectly performed between the external device 32 and the display device 4 via the portable recording medium 5, so that the subject 1 is allowed to move freely during the imaging unlike a case where the external device 32 and the display device 4 are directly connected to each other by wire.

Configuration of Storage Case

Figure 4:
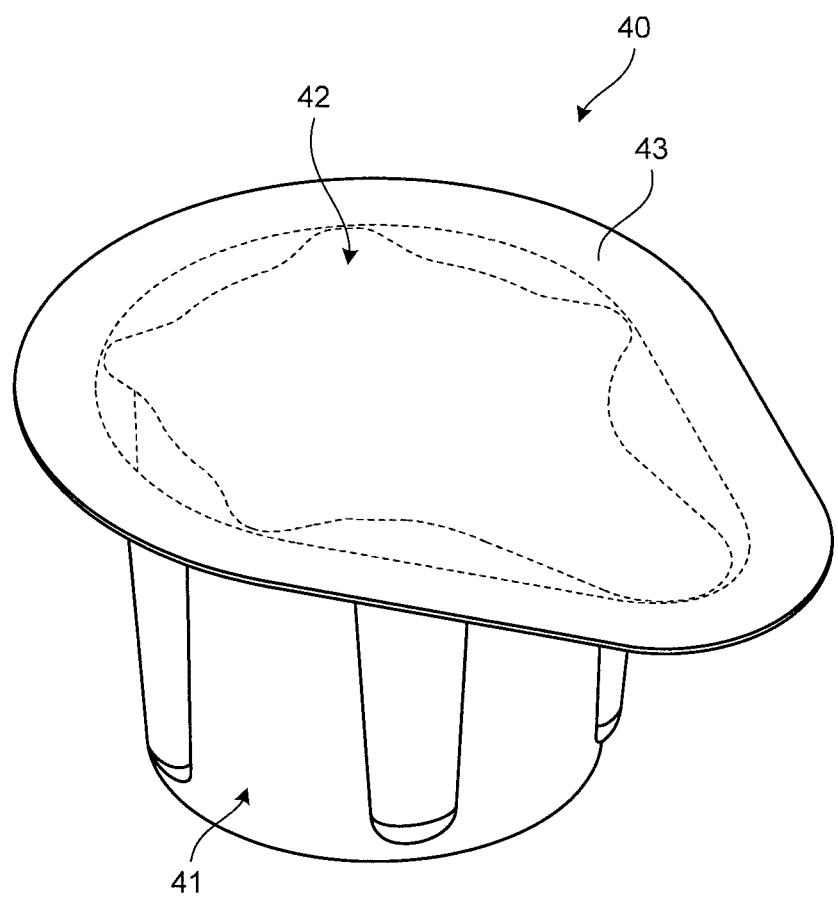
FIG. 4 is a perspective view of a configuration of a storage case that accommodates the capsule endoscope shown in FIG. 2.
Figure 5:
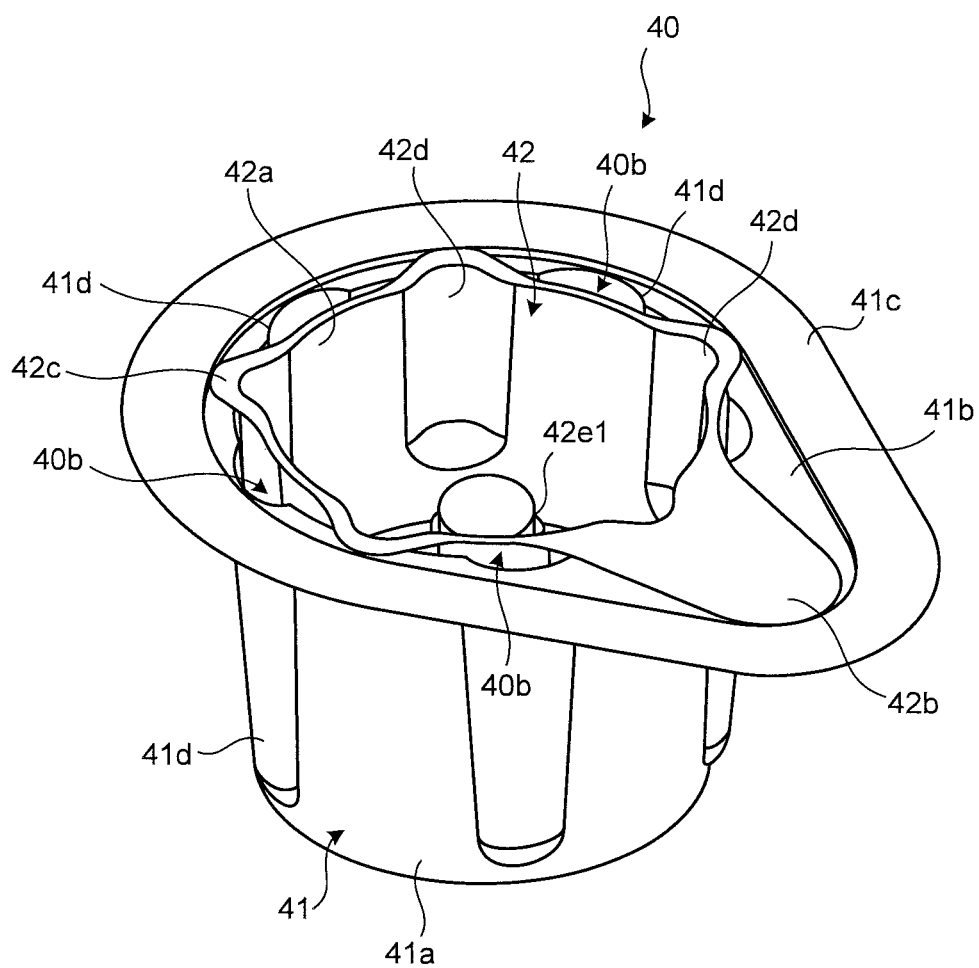
FIG. 5 is a perspective view of a state where a sterilization sheet is removed from the storage case shown in FIG. 4.
Figure 6:
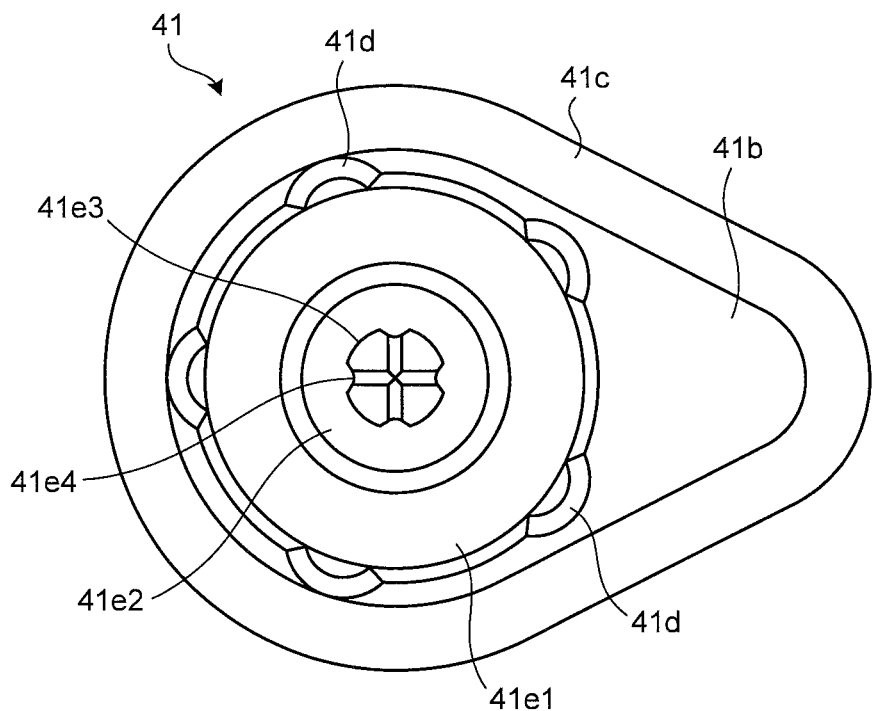
FIG. 6 is a top view of a top surface of the storage case shown in FIG. 5.
Figure 7:
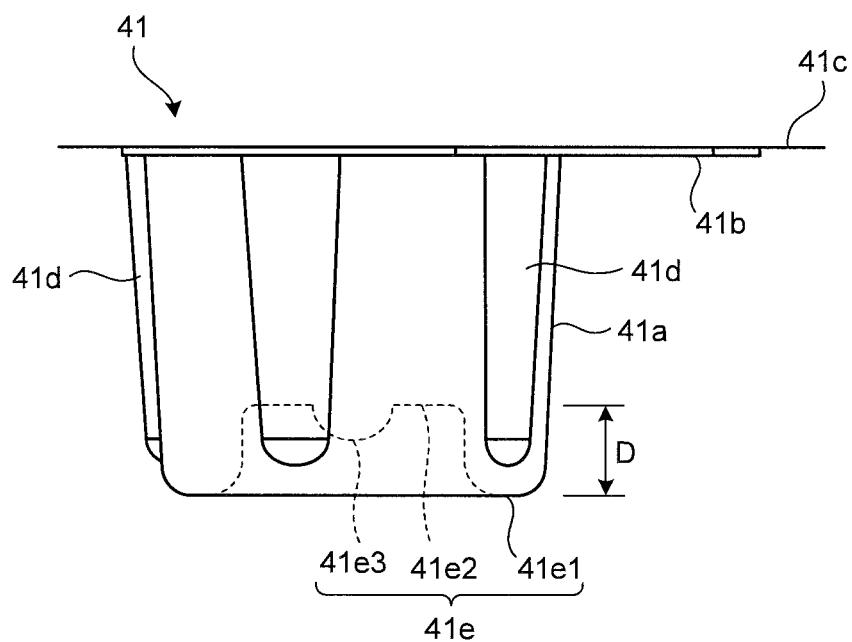
FIG. 7 is a side view of a side surface of the storage case shown in FIG. 5.
Figure 8:
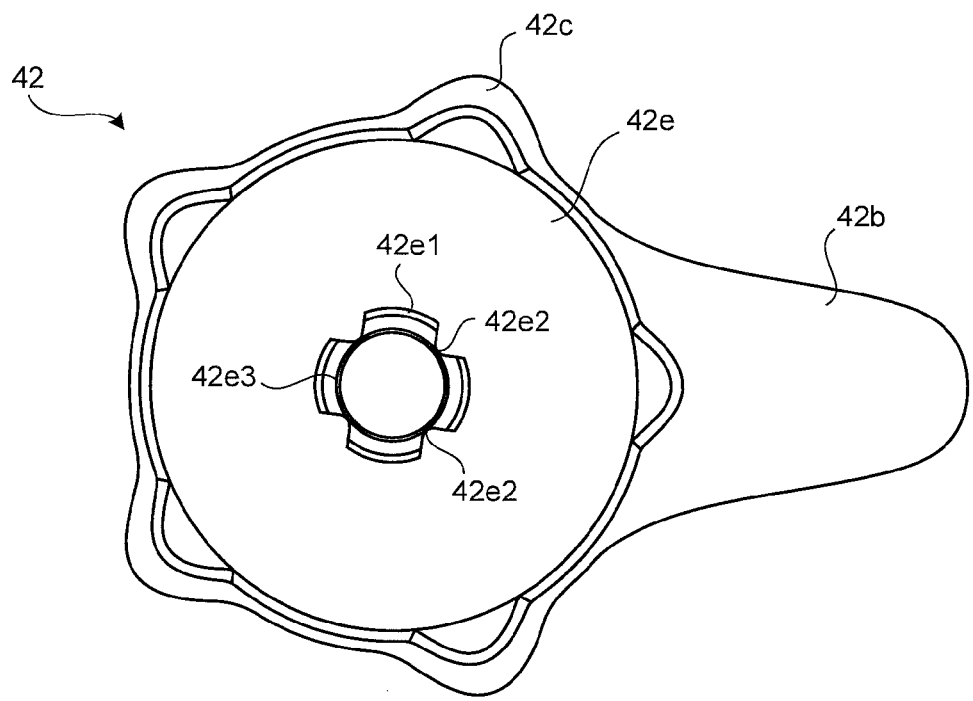
FIG. 8 is a top view of a top surface of the inner cover part shown in FIG. 5.
Figure 9:
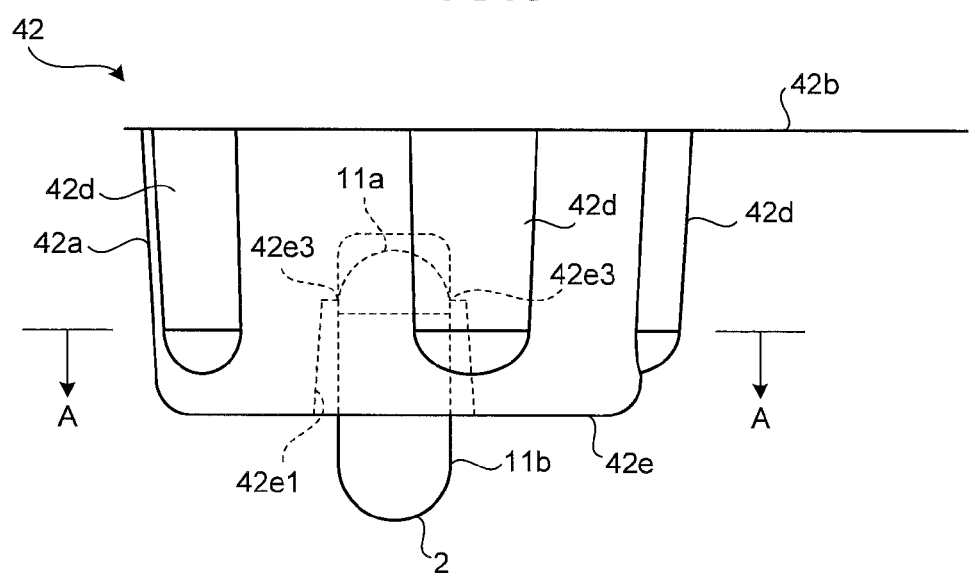
FIG. 9 is a side view of a side surface of the inner cover part shown in FIG. 5.
Figure 10:
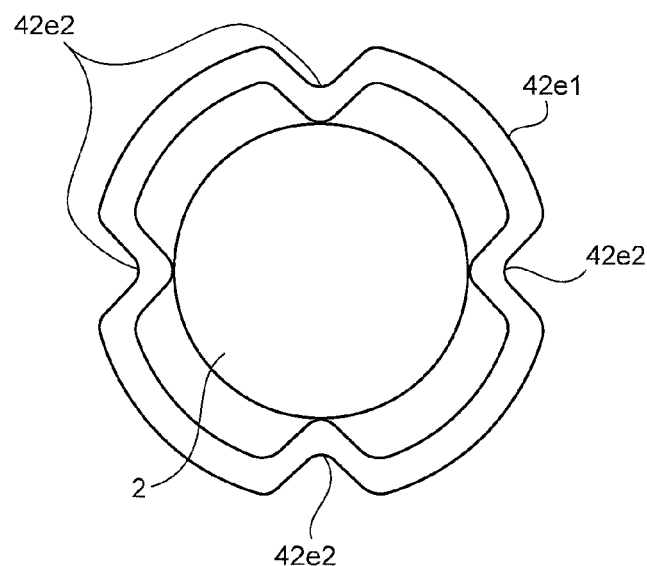
FIG. 10 is a cross-sectional view along a line A-A in FIG. 9.
Figure 11:
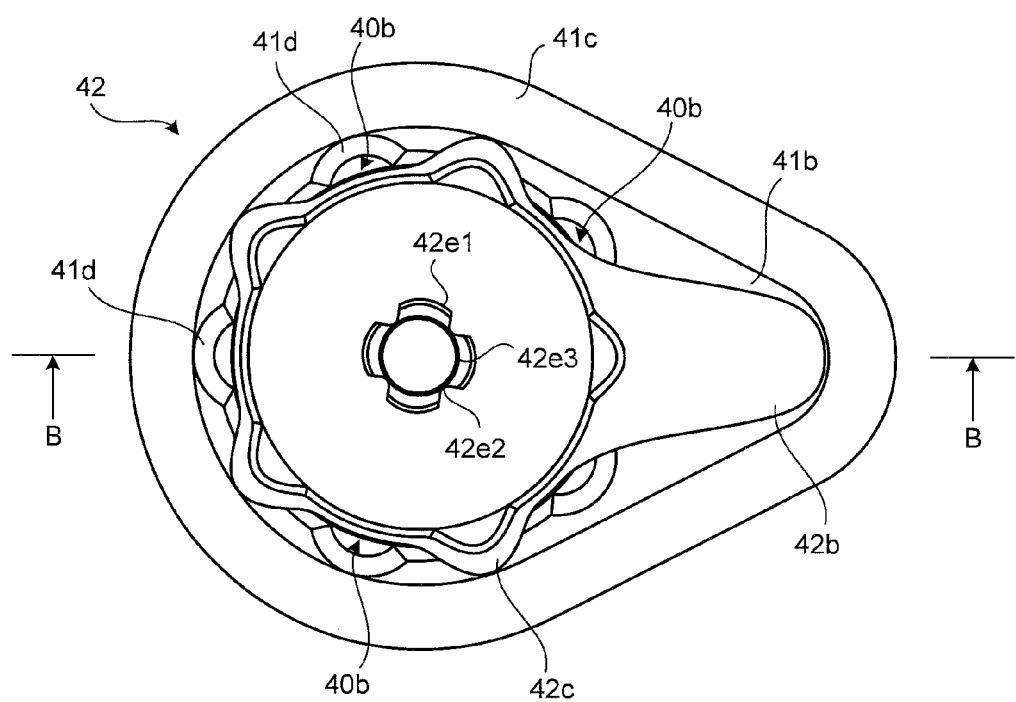
FIG. 11 is a top view of a top surface of the storage case shown in FIG. 5.
Figure 12:
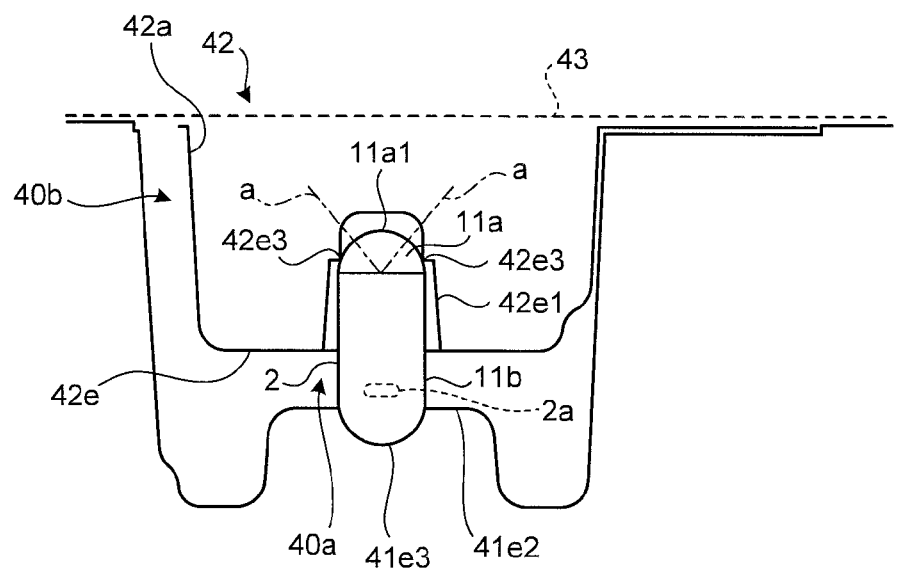
FIG. 12 is a cross-sectional view along a line B-B in FIG. 11.
Figure 13:
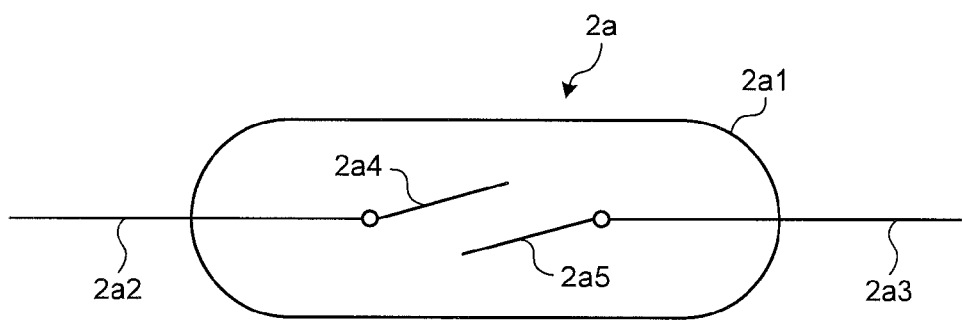
FIG. 13 is a pattern diagram of a configuration of the reed switch shown in FIG. 12.
Figure 14:
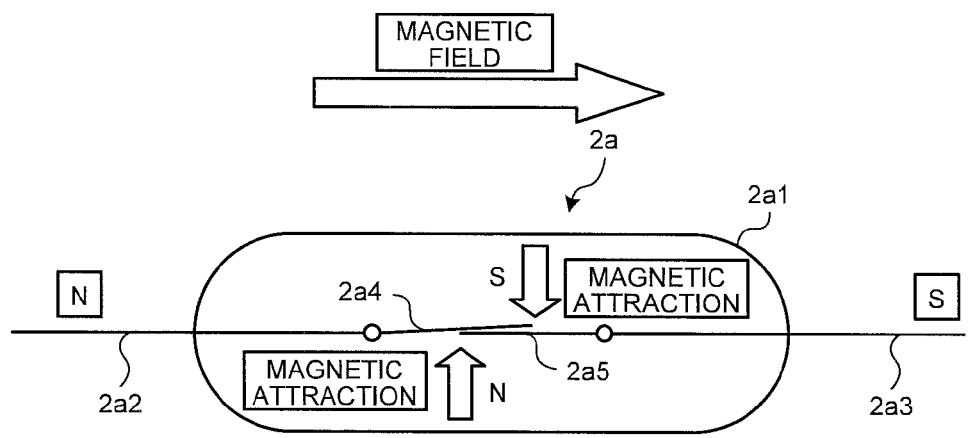
FIG. 14 is a pattern diagram of a configuration of the reed switch when a magnetic field is applied.
Figure 15:
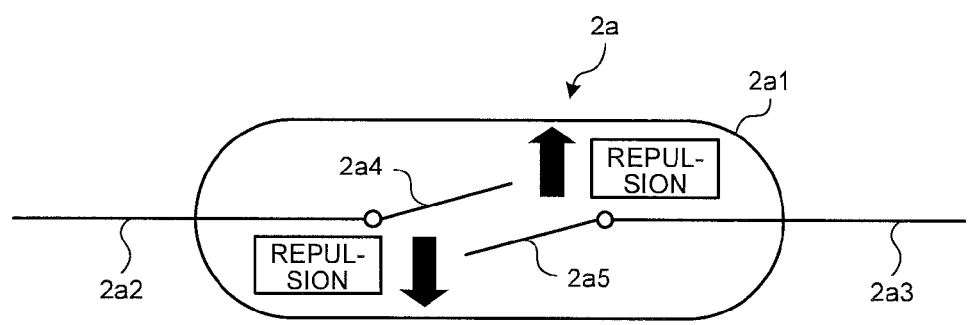
FIG. 15 is a pattern diagram of a configuration of the reed switch when the applied magnetic field becomes low in intensity.
Figure 16:
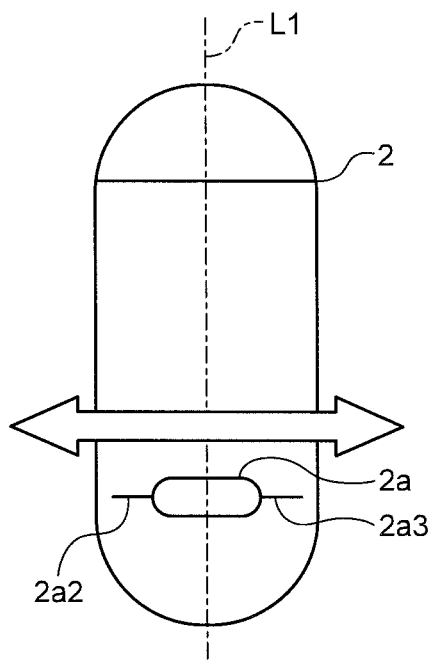
FIG. 16 is a pattern diagram for explaining an arrangement position of the reed switch in the inside of the capsule endoscope.
Figure 17:
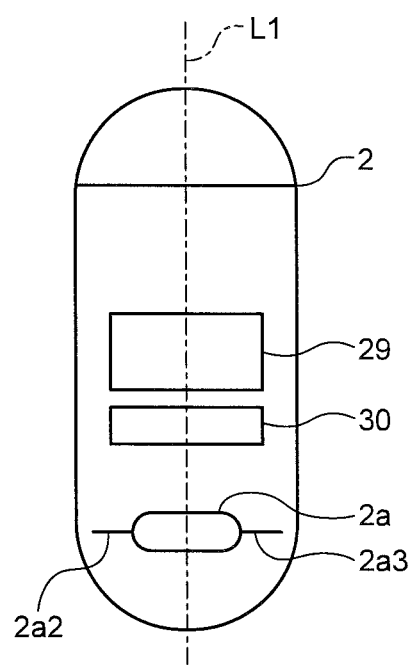
FIG. 17 is a pattern diagram for explaining an arrangement position of the reed switch in the inside of the capsule endoscope.

The capsule endoscope 2 needs to be sterilized before use and be kept sterilized. Accordingly, the capsule endoscope 2 is accommodated in a storage case which can be sterilized in this embodiment. A configuration of the storage case will be explained below with reference to FIGS. 4 to 17. FIG. 4 is a perspective view of a configuration of the storage case that accommodates the capsule endoscope shown in FIG. 2. FIG. 5 is a perspective view of a state where a sterilization sheet is removed from the storage case shown in FIG. 4. FIG. 6 is a top view of a top surface of the storage case shown in FIG. 5. FIG. 7 is a side view of a side surface of the storage case shown in FIG. 5. FIG. 8 is a top view of a top surface of the inner cover part shown in FIG. 5. FIG. 9 is a side view of a side surface of the inner cover part shown in FIG. 5. FIG. 10 is a cross-sectional view along a line A-A in FIG. 9. FIG. 11 is a top view of a top surface of the storage case shown in FIG. 5. FIG. 12 is a cross-sectional view along a line B-B in FIG. 11. FIG. 13 is a pattern diagram of a configuration of the reed switch shown in FIG. 12. FIG. 14 is a pattern diagram of a configuration of the reed switch when a magnetic field is applied. FIG. 15 is a pattern diagram of a configuration of the reed switch when the applied magnetic field becomes low in intensity. FIG. 16 is a pattern diagram for explaining an arrangement position of the reed switch in the inside of the capsule endoscope. FIG. 17 is a pattern diagram for explaining an arrangement position of the reed switch in the inside of the capsule endoscope.

As shown in FIGS. 4 and 5, the storage case 40 is provided with a blister pack 41 that is formed by an outer storage part capable of accommodating therein the capsule endoscope 2, an inner cover part 42 that is arranged in the blister pack 41 and formed by an inner storage part that retains the capsule endoscope 2 with the blister pack 41, and a sterilization sheet 43 that is provided on a top surface of the blister pack 41 to block an opening of the blister pack 41. The blister pack 41 and the inner cover part 42 are formed by processing polypropylene and the like via a forming process such as a vacuum forming.

As shown in FIGS. 6 and 7, the blister pack 41 is provided with a cylindrical part 41a having a bottom, a tongue-shaped handgrip part 41b provided on a part of an upper edge of an opening of the cylindrical part 41a, an edge part 41c provided on the upper edge of the opening of the cylindrical part 41a and an outer circumference of the handgrip part 41b, and a plurality of semi-cylindrical projection parts 41d that are provided on a circumferential surface of the cylindrical part 41a in a manner of projecting from the inside to the outside of the cylindrical part 41a.

The cylindrical part 41a has a bottom face 41e, which is formed by an outside bottom face 41e1 provided on the circumference side of the cylindrical part 41a and an inside bottom face 41e2 provided at the approximate center part of the outside bottom face 41e1. The inside bottom face 41e2 is formed in a disk shape having a predetermined radius, and the outside bottom face 41e1 has a bottom face protruding from the position of the inside bottom face 41e2 to the outside (in the direction opposite to the opening) of the cylindrical part 41a and is formed in a hollow donut shape having a predetermined width on its lower surface. A height difference D is formed between the outside bottom face 41e1 and the inside bottom face 41e2 as shown in FIG. 7. A semi-spherical retaining part 41e3 sagging from the position of the inside bottom face 41e2 toward the outside bottom face 41e1 is formed at the center part of the inside bottom face 41e2. The retaining part 41e3 serves to retain the dome-shaped rear end part constituting the body cover 11b of the capsule endoscope 2 and is provided with a cross-shaped projection part 41e4 in the inside toward the opening, thereby allowing sterilizing gas to get into the rear end part of the body cover 11b retained in a line contact manner and to uniformly sterilize the entire rear end part. The projection part 41e4 may include a plurality of projections to retain the rear end part of the capsule endoscope 2 in a point contact manner.

The handgrip part 41b is formed of a plate member having an approximately triangular top surface, on which a handgrip part 42b, to be explained later, of the inner cover part 42 can abut as shown in FIG. 5. The edge part 41c has a predetermined width and is formed in a step shape higher by one step on the upper edge of the opening of the cylindrical part 41a and the outer circumference of the handgrip part 41b to suppress the movement of the handgrip part of the inner cover part 42 abutting on the handgrip part 41b. The height of the edge part 41c is configured to be equal to or more than the thickness of the handgrip part 42b and an edge part 42c of the inner cover part 42 abutting on the handgrip part 41b, which enables the sterilization sheet 43 to be attached to the top surface of the edge part 41c in the state where the inner cover part 42 is accommodated in the blister pack 41.

The projection parts 41d are approximately semi-cylindrical projections formed in a longitudinal direction of the cylindrical part 41a, a diameter is the largest at an upper end (at the opening side of the cylindrical part 41a) and gradually decreases as it goes toward the lower end (toward the bottom face 41e side), and the projection parts 41d having the same shape are arranged along the longitudinal direction of the cylindrical part 41a at approximately regular intervals. In each projection part 41d, the upper end is opened and the lower end forms a semi-dome-shaped bottom face. In this embodiment, five projection parts 41d are provided on the circumferential surface of the cylindrical part 41a at approximately regular intervals.

As shown in FIGS. 8 and 9, the inner cover part 42 is provided with a cylindrical part 42a having a bottom, the tongue-shaped handgrip part 42b provided on a part of an upper edge of an opening of the cylindrical part 42a, an edge part 42c provided on the upper edge of the opening of the cylindrical part 42a in a manner of extending from the handgrip part 42b, and a plurality of semi-cylindrical projection parts 42d projecting from the inside to the outside direction of the cylindrical part 42a.

As shown in FIGS. 8 to 12, the cylindrical part 42a has a bottom face 42e and a protrusion part 42e1 having a hole for retaining the capsule endoscope 2 is formed at the center part of the bottom face 42e. The protrusion part 42e1 is formed to have, in section, an approximately cylindrical convex shape having a top surface protruding toward the inside (toward the opening) of the cylindrical part 42a from the position of the bottom face 42e and an inner diameter thereof is configured to be slightly larger than the outer diameter of the capsule endoscope 2. A plurality of, four in this embodiment, straight-line shaped projections 42e2 are formed in the longitudinal direction toward the opening of the protrusion part 42e1 in an inner circumference of the protrusion part 42e1. A step part 42e3 is provided on t top surface side of the protrusion part 42e1 and an inner diameter of the step part 42e3 is configured to be smaller than an inner diameter at the opening side of the protrusion part 42e1. As shown in FIG. 12, the bottom face 42e including the protrusion part 42e1 of the cylindrical part 42a and the inside bottom face 41e2 including the retaining part 41e3 of the blister pack 41 enable accommodating and retaining the capsule endoscope 2 when the inner cover part 42 is accommodated in the blister pack 41.

As shown in FIGS. 9 and 12, when the front head cover 11a of the capsule endoscope 2 is inserted into the protrusion part 42e1, the projections 42e2 retain a part of the body cover 11b of the airtight container 11 in a line contact manner and an end part of the step part 42e3 retains a part of the front head cover 11a in a line contact manner so that the mirror-finished part 11a1 within the range of the dashed line indicated by a and a is not in contact with parts, including the projections 42e2 and the step part 42e3, of the protrusion part 42e1. The projections 42e2 are not limited to the example of being formed straightly in the longitudinal direction of the protrusion part 42e1 and a plurality of projections may be provided in the protrusion part 42e1 to retain respective part of the body cover 11b of the airtight container 11 in a point contact manner.

The handgrip part 42b is formed of an approximately triangular plate member a top surface of which is approximately smaller than the handgrip part 41b and is formed integrally with the edge part 42c formed on the upper edge of the opening of the cylindrical part 41a, as shown in FIGS. 8 and 11. The handgrip part 42b is configured to abut on the handgrip part 41b of the blister pack 41 when the inner cover part 42 is accommodated in the blister pack 41. The edge part 42c is formed on the upper edge of the opening of the cylindrical part 42a and is configured to abut on the upper edge of the opening of the blister pack 41 when the inner cover part 42 is accommodated in the blister pack 41. As explained above, the thickness of the handgrip part 42b and the edge part 42c is configured to be equal to or smaller than the thickness of the edge part 41c of the blister pack 41. When the inner cover part 42 is accommodated in the blister pack 41, the movement of the handgrip part 42b is limited to the width of the handgrip part 41b by the edge part 41c, and when the sterilization sheet 43 is attached to the top surface of the edge part 41c, the entirety of the inner cover part 42 including the handgrip part 42b and the edge part 42c is accommodated in the blister pack 41.

The projection parts 42d are approximately semi-cylindrical projections provided in the longitudinal direction of the cylindrical part 42a and provided at approximately regular intervals along the longitudinal direction of the cylindrical part 42a. In each projection part 42d, an upper end is opened and the lower end forms a semi-dome-shaped bottom face. In this embodiment, five projection parts 42d are arranged on the circumferential surface of the cylindrical part 42a at approximately regular intervals. The projection parts 42d are formed at respective positions not facing respective projection parts 41d of the blister pack 41 and in a manner that the most projecting portions of the projection parts 42d can be in contact with an inner circumferential surface of the cylindrical part 41a in the state where the inner cover part 42 is accommodated in the blister pack 41 and the handgrip parts 41b and 42b are in direct contact with each other, thereby preventing a bumpy movement of the inner cover part 42 in the blister pack 41.

As shown in FIGS. 5, 11, and 12, a passage 40b is formed between the inner circumferential surface of the projection parts 41d of the blister pack 41 and the outer circumferential surface of the cylindrical part 42a of the inner cover part 42, thereby transmitting the sterilizing gas coming from the outside through the sterilization sheet 43. The passage 40b and a retention space area 40a communicate with each other, thereby allowing the sterilizing gas having passed through the passage 40b to reach the retention space area 40a.

As shown in FIG. 12, the capsule endoscope 2 is provided therein with a power-supplying reed switch 2a, which performs an ON/OFF operation depending on a magnetic field from the outside, and notifies to the outside that the reed switch 2a becomes an ON state and the power is supplied to each function executing unit by a blink of the LED 20 shown in FIG. 2. As shown in FIG. 13, the reed switch 2a is formed by a cylindrical member 2a1 and reed terminals 2a2 and 2a3 extend in a manner of penetrating along a central axis from both end parts in a long axis direction of the cylindrical member 2a1. The reed terminals 2a2 and 2a3 are respectively connected to sensitive movers 2a4 and 2a5 in an inside of the cylindrical member 2a1. The sensitive movers 2a4 and 2a5 are arranged away not to be in contact with each other in a normal state. The reed terminals 2a2 and 2a3 and the sensitive movers 2a4 and 2a5 are conductive bodies and also magnetic bodies.

When a magnetic field is applied to the reed switch 2a having this configuration in the extending direction (sensitivity direction in the magnetic field) of the reed terminals 2a2 and 2a3 as shown in FIG. 14, the reed terminals 2a2 and 2a3 become magnetized. On this occasion, the sensitive movers 2a4 and 2a5 are magnetized to different polarities from each other. Thus, a magnetic attraction works between the sensitive movers 2a4 and 2a5 and the sensitive movers 2a4 and 2a5 become in contact. By the contact of the sensitive movers 2a4 and 2a5, the reed terminals 2a2 and 2a3 are electrically conducted. When the magnetic field applied to the reed switch 2a becomes low in intensity, the sensitive movers 2a4 and 2a5 become away from each other as shown in FIG. 15 due to a repulsion derived from a spring property of the sensitive movers 2a4 and 2a5, and thereby the reed terminals 2a2 and 2a3 are electrically insulated. In this manner, the reed switch 2a functions as an electrical switch that performs an ON/OFF switching in response to the application and the stoppage of the magnetic field in the extending direction of the reed terminals 2a2 and 2a3.

As shown in FIG. 16, the reed switch 2a is provided in the inside of the capsule endoscope 2 so that the reed terminals 2a2 and 2a3 extend in a direction perpendicular to a central axis L1 of the capsule endoscope 2. By this configuration, when a magnetic field which is perpendicular to the central axis L1 of the capsule endoscope 2 and parallel to the extending direction (a direction indicated by an arrow in FIG. 16) of the reed terminals 2a2 and 2a3 is applied, the reed switch 2a becomes an ON state and the power is supplied to each function executing unit. The reason why the reed switch 2a is arranged in this direction is because the reed switch 2a is arranged on a substrate having a disk shape stretching out to the radial direction of the capsule endoscope 2 or a similar shape, similarly to parts such as the CCD 22 and the RF transmitting unit 24 shown in FIG. 2 in the inside of the capsule endoscope 2.

As shown in FIG. 17, a magnet 30 for controlling the position and the direction of the capsule endoscope 2 in response to an external magnetic field is provided in addition to the battery 29 in the inside of the capsule endoscope 2. The weight of these parts is heavy compared to other parts arranged in the inside of the capsule endoscope 2. Therefore, these parts are arranged around a central part of the capsule endoscope 2 to prevent a position of the center of gravity of the capsule endoscope 2 from being biased. The reed switch 2a the weight of which is lighter than that of these parts is thus arranged around an end part of the capsule endoscope 2. When the magnet 30 is arranged in the inside of the capsule endoscope 2, it is necessary to arrange the reed switch 2a away from the magnet 30 to reduce an influence of the magnet 30 on the reed switch 2a. Because of the reason explained above, the reed switch 2a is arranged at a position close to the end part of the capsule endoscope 2 and locates lower than the position of the bottom face 42e of the inner cover part 42 in the state where the capsule endoscope 2 is accommodated in the storage case as shown in FIG. 12. This arrangement similarly applies to a case where the guidance of the capsule endoscope 2 is not performed and the magnet 30 is not mounted.

In using the capsule endoscope 2, a medical staff removes the sterilization sheet 43 from the storage case 40 and inserts the power source starter 7 to the inside of the cylindrical part 42a of the inner cover part 42. The reed switch 2a thus switches the driving of the capsule endoscope 2 from OFF state to ON state by the magnetic force generated by the magnet in the power source starter 7. The medical staff is able to check the driving state of the capsule endoscope 2 by checking a blink state of the LED 20 through the protrusion part 42e1 having a transparence or a translucence.

Configuration of Power Source Starter

Figure 18:
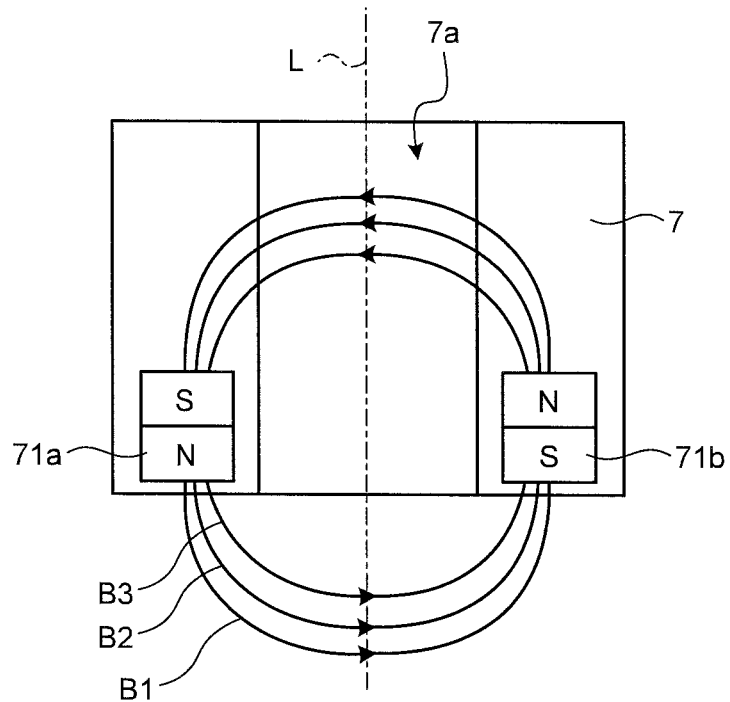
FIG. 18 is a cross-sectional view of a configuration of the power source starter shown in FIG. 1.
Figure 19:
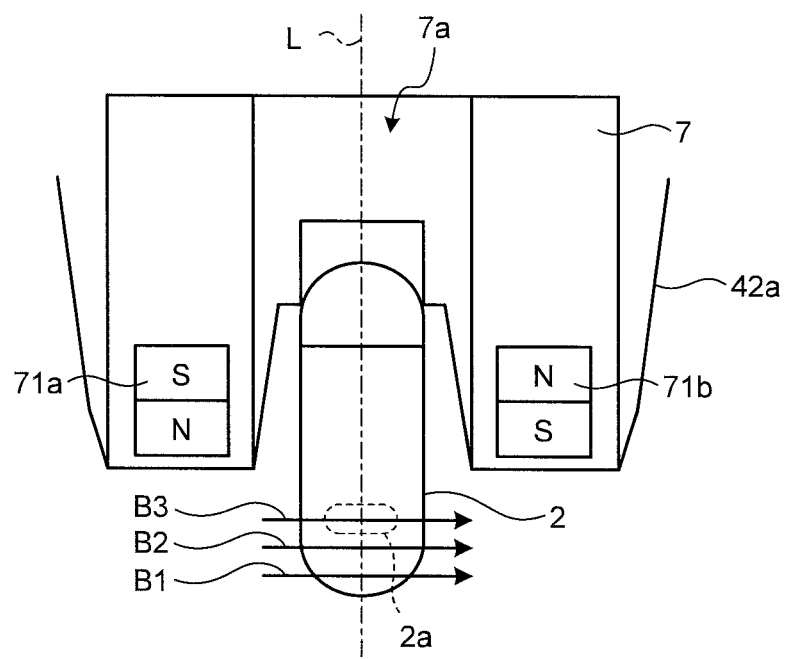
FIG. 19 is an explanatory cross-sectional view of a method of applying a magnetic field to the reed switch by using the power source starter shown in FIG. 18.
Figure 20:
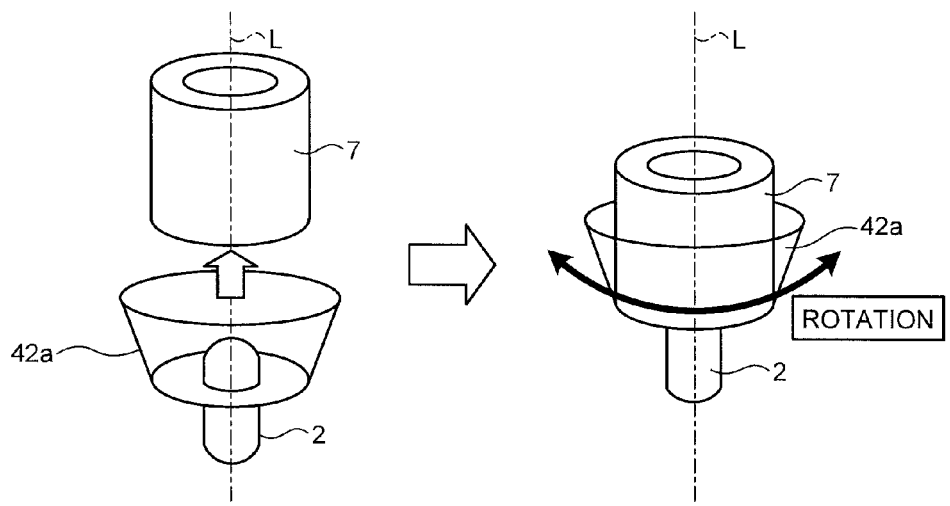
FIG. 20 is a pattern diagram for explaining a method of matching a direction of magnetic force lines generated by the power source starter shown in FIG. 18 and a direction of sensitivity of the reed switch.
Figure 21:
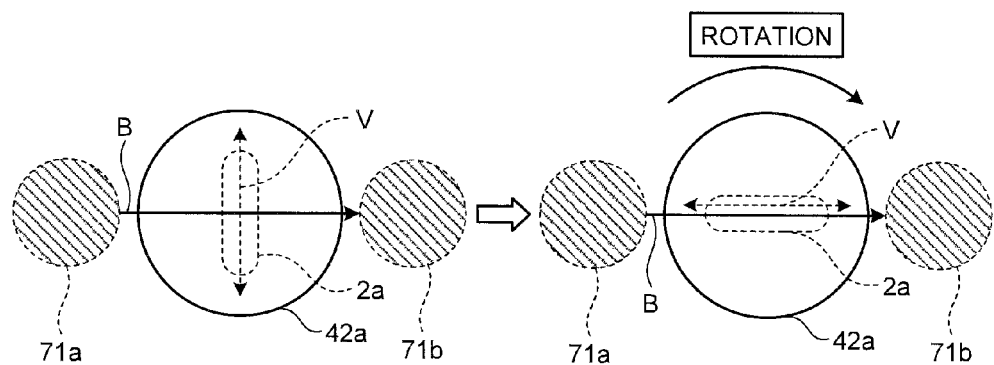
FIG. 21 is a pattern diagram for explaining a method of matching the direction of magnetic force lines generated by the power source starter shown in FIG. 18 and the direction of sensitivity of the reed switch.

A configuration and an operating method of the power source starter 7 will be explained with reference to FIGS. 18 to 21 next. FIG. 18 is a cross-sectional view of a configuration of the power source starter shown in FIG. 1. FIGS. 19 to 21 are explanatory views of a method of switching the driving of the capsule endoscope from OFF state to ON state by using the power source starter shown in FIG. 18.

As shown in FIG. 18, the power source starter 7 is formed of a cylindrical member having a penetration hole 7a which serves as an insertion part extending in a direction of a central axis L according to the present invention. Besides, magnets 71a and 71b which are formed by a permanent magnet or an electromagnet and have a column shape are buried at positions between which the central axis L in the cylindrical member is sandwiched. The magnets 71a and 71b generate magnetic force lines in different directions. Specifically, while the magnet 71a generates magnetic force lines downward in the figure, the magnet 71b generates magnetic force lines upward in the figure. In other words, the magnets 71a and 71b constitute a magnetic circuit that generates a plurality of magnetic force lines intersecting with the central axis L along the direction of the central axis L. The magnetic circuit generates magnetic force lines which are substantially symmetric about the central axis L as an axis of symmetry in any planar surfaces including the central axis L.

As explained, the reed switch 2a in the capsule endoscope 2 locates at a position lower than the position of the bottom face 42e of the inner cover part 42. Therefore, the reed switch 2a locates in an outside of an edge part of the cylindrical member of the power source starter 7 even when the power source starter 7 is inserted into the inner cover part 42. However, an action of at least one of the plurality of magnetic force lines B1 to B3 generated by the magnets 71a and 71b on the reed switch 2a causes the driving of the capsule endoscope 2 to be switched from OFF state to ON state as shown in FIG. 19. Thus, since it becomes unnecessary according to the power source starter 7 to adjust the position of the magnets 71a and 71b and the position of the reed switch 2a substantially within the same planar surface in applying a magnetic field to the reed switch 2a, it is possible to easily apply a magnetic field to the reed switch 2a and switch the driving of the capsule endoscope 2 from OFF state to ON state even when the reed switch 2a locates outside the power source starter 7.

When the sensitivity direction of the reed switch 2a does not match the direction of the plurality of magnetic force lines B1 to B3 generated by the magnets 71a and 71b, it is preferable to rotate the storage case 40 to rotate the cylindrical part 42a with respect to the power source starter 7 as shown in FIG. 20. By this method, the capsule endoscope 2 and the reed switch 2a are rotated in accordance with the rotation of the cylindrical part 42a, so that a sensitivity direction V of the reed switch 2a matches the direction of the magnetic field line B generated by the magnets 71a and 71b as shown in FIG. 21 and the driving of the capsule endoscope 2 can be surely switched from OFF state to ON state.

Figure 22:
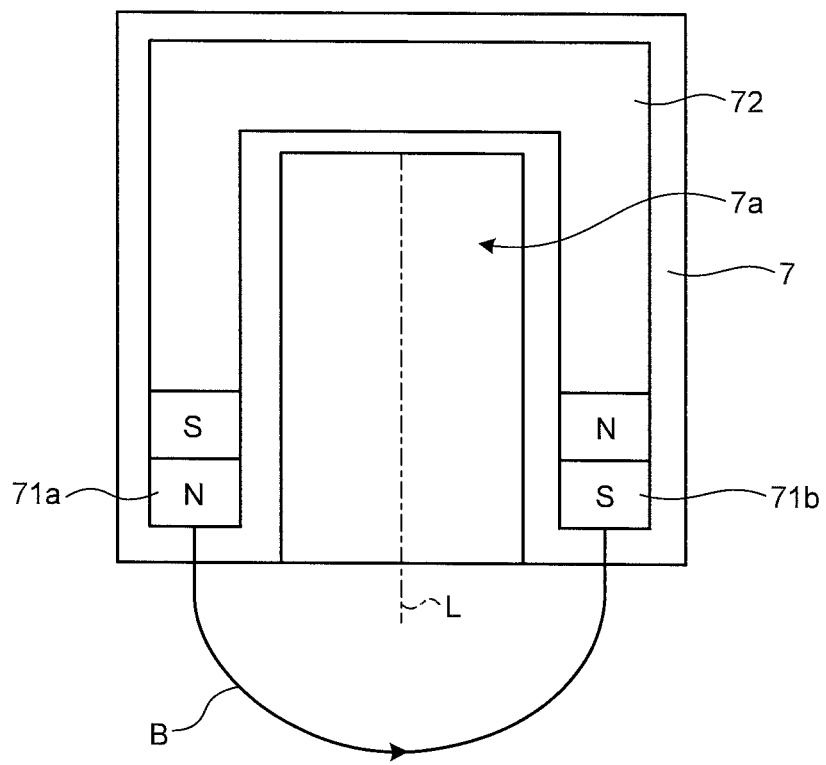
FIG. 22 is a cross-sectional view of a configuration of a modification example of the power source starter shown in FIG. 19.

While the magnetic circuit generating a plurality of magnetic field lines intersecting with the central axis L along the direction of the central axis L is configured by burying two magnets 71a and 71b at positions between which the central axis L in the cylindrical member is sandwiched in this embodiment, the magnetic circuit generating a plurality of magnetic force lines intersecting with the central axis L along the direction of the central axis L may be configured by connecting the magnets 71a and 71b by a magnetic body 72 to form an integral magnet with the magnets 71a and 71b as shown in FIG. 22, for example. Alternatively, one magnet having the same shape as that configured by the magnets 71a and 71b and the magnetic body 72 may be used. By this configuration, it becomes possible to increase the number of magnetic force lines intersecting with the central axis L and thereby to apply a magnetic field to the reed switch 2a more easily.

Figure 23:
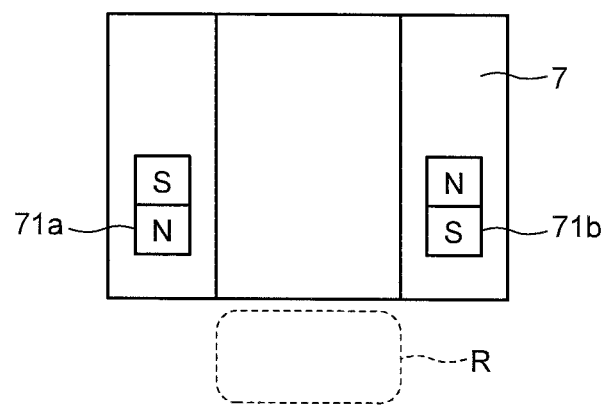
FIG. 23 shows a magnetic field region in which the power source starter is capable of activating the reed switch of the capsule endoscope.
Figure 24A:
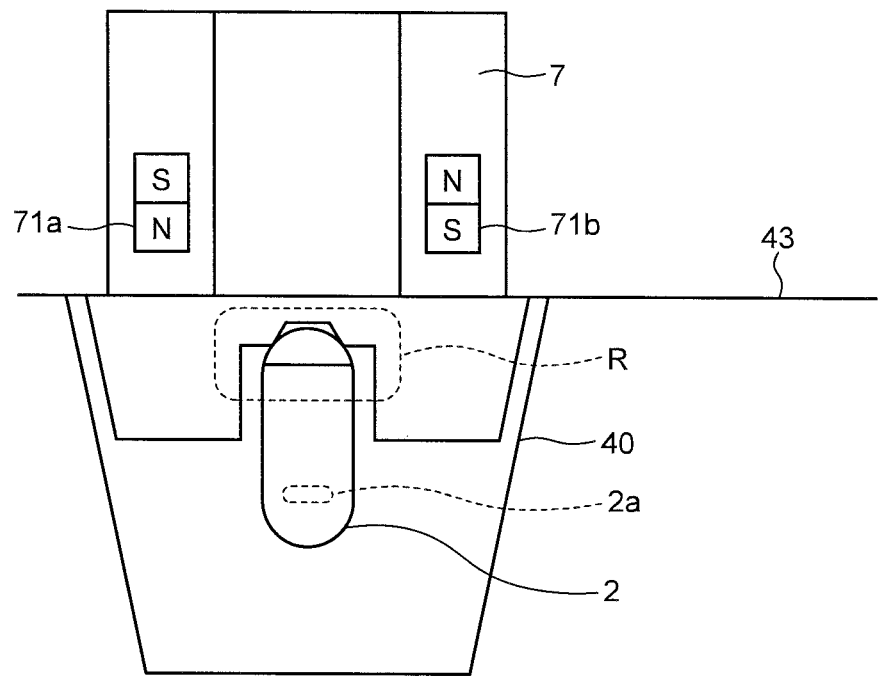
FIGS. 24A and 24B are pattern diagrams of a state where the power source starter is put close to the storage case under a condition that the sterilization sheet is not removed from the storage case.
Figure 24B:
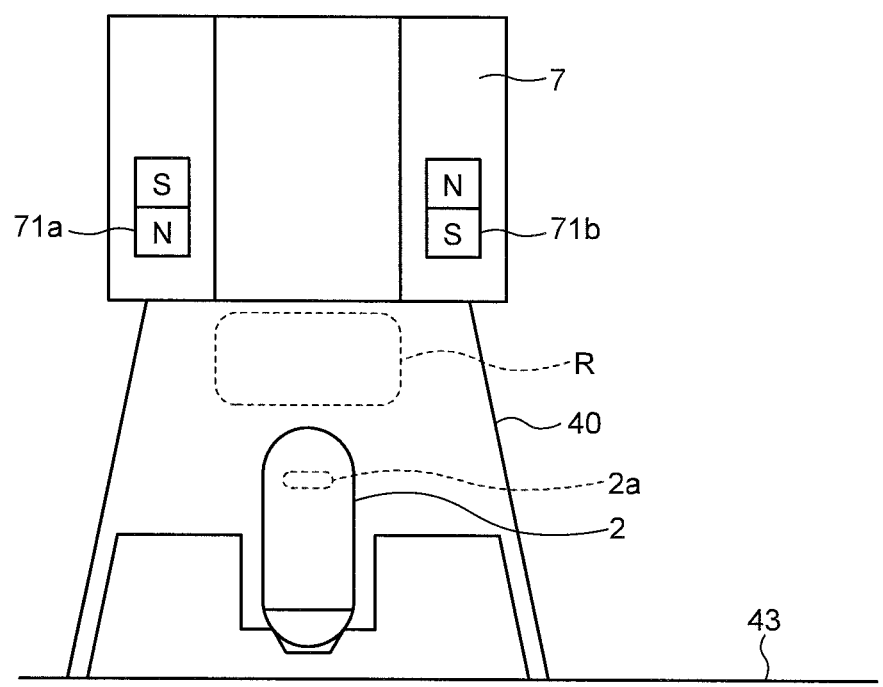

In the power source starter 7 configured in this manner, an intensity of the magnetic field generated by the magnets 71a and 71b becomes lowered sharply when it is away in distance. Therefore, a magnetic field region R in which the power source starter 7 is able to operate the reed switch 2a of the capsule endoscope 2 is formed only in a neighborhood region of the power source starter 7 as shown in FIG. 23. Thus, it is possible, depending on the dimension, material, and position of the magnets 71a and 71b and the design of the storage case 40, that, even when the power source starter 7 is put close to the storage case 40, the driving of the capsule endoscope 2 is configured not to be switched to ON state under the condition that the sterilization sheet 43 is not removed from the storage case 40. Specifically, it is possible even when the storage case 40 is wrongly put close to the power source starter 7 as shown in FIGS. 24A and 24B to prevent the driving of the capsule endoscope 2 from being switched to ON state as long as the sterilization sheet 43 is not removed from the storage case 40 and the reed switch 2a locates outside the magnetic field region R.

While the embodiment to which the invention achieved by the inventor is applied is explained so far, the present invention is not limited by the description and the drawings, which are merely a part of the disclosure of the present invention, according to the embodiment. While the power source starter 7 in this embodiment is configured to be fixed to the frame body constituting the display device 4 to suppress a possibility of being attracted by a magnetic force generated when used in combination with a magnetic force generator such as a magnetic guidance device, the power source starter 7 may not be fixed to the frame body but be portable, for example. In this way, other exemplary embodiments and examples, practical techniques, and the likes to be made by those skilled in the art based on the present embodiment will be included within a scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule-medical-device dedicated power source starter that allows switching, by an application of a magnetic field to a magnetic switch that is provided in an inside of a capsule medical device and has a particular sensitivity direction in the magnetic field, a driving of the capsule medical device from an OFF state to an ON state, comprising:

a cylindrical member having an insertion part that is formed along a central axis direction and to which the capsule medical device is inserted so that a longitudinal axis direction of the capsule medical device is along the central axis direction; and a magnetic circuit that generates magnetic force lines which corresponds to the magnetic field and are substantially symmetric about the central axis as an axis of symmetry in any planar surfaces including the central axis of the insertion part, wherein the magnetic circuit includes a pair of magnets which are arranged to sandwich the central axis and which generate the magnetic force lines that intersect with the central axis, the pair of magnets are arranged so as to generate one of the magnetic force lines that runs from one end of one of the pair of magnets in a direction along the central axis and intersects with the central axis towards one end of the other of the pair of magnets, and to generate the other of magnetic force lines that runs from the other end of the other of the pair of magnets and intersects with the central axis towards the other end of the one of the pair of magnets, and when the capsule medical device is inserted in the insertion part, one of the magnetic force lines, which runs from one end of one of the pair of magnets and intersects with the central axis, passes through the magnetic switch which is located outside of an edge part of the cylindrical member.

2. The capsule-medical-device dedicated power source starter according to claim 1, wherein the pair of magnets are permanent magnets.

3. The capsule-medical-device dedicated power source starter according to claim 1, wherein the pair of magnets are electromagnets.

4. The capsule-medical-device dedicated power source starter according to claim 1, wherein the insertion part has a cylindrical shape in which the capsule medical device is able to rotate around a rotation axis which is along the central axis direction.

5. The capsule-medical-device dedicated power source starter according to claim 1, comprising a magnetic body connecting the pair of magnets.

* * * * *